United States Patent [19]

Marks et al.

[11] Patent Number: 5,500,398
[45] Date of Patent: Mar. 19, 1996

[54] HOMOGENEOUS α-OLEFIN DIMERIZATION CATALYSTS

[75] Inventors: Tobin J. Marks; Xinmin Yang, both of Evanston, Ill.

[73] Assignee: Northwestern University, Evanston, Ill.

[21] Appl. No.: 336,864

[22] Filed: Nov. 9, 1994

[51] Int. Cl.$^6$ .................................................. B01J 31/38
[52] U.S. Cl. ......................... 502/103; 502/117; 502/152; 585/510
[58] Field of Search ..................... 502/103, 117, 502/152; 585/510

[56] References Cited

U.S. PATENT DOCUMENTS

| | | | |
|---|---|---|---|
| 5,132,262 | 7/1992 | Rieger et al. | 502/117 |
| 5,276,238 | 1/1994 | Doyle | 585/511 |
| 5,281,679 | 1/1994 | Jejelowo et al. | 526/114 |

FOREIGN PATENT DOCUMENTS 0427697  5/1991  European Pat. Off. .

OTHER PUBLICATIONS

Yang et al. "Cation–like" Homogenous Olefin Polymerization Catalysts Based upon Zirconocene Alkylo and Tris(pentafluorophenyl)borane, J. Chem. Soc. 1991, 113, pp. 3623–3625.

*Primary Examiner*—E. Rollins Cross
*Assistant Examiner*—Timothy H. Meeks
*Attorney, Agent, or Firm*—Welsh & Katz, Ltd.

[57] ABSTRACT

A new class of olefin dimerization catalysts and an efficient method for their preparation is disclosed. $B(C_6F_5)_3$ reacts quantitatively with Group 4 metallocene type catalysts to yield highly reactive cationic complexes as follows:

$(L_2MR^2)^+X^-$ where
L=$R_2(C_5H_3)$; R=a $C_3$–$C_{20}$ tert-alkyl group; $R^2$=a $C_1$–$C_{20}$ alkyl group, H
M=Ti, Zr, Hf;
$X^-$=$RB(C_5F_3)^-_3$, or methylalumoxane, where R"=a $C_1$–$C_{20}$ alkyl group, H.

These complexes are potent catalysts and may be used in the dimerization of α-olefins.

2 Claims, 1 Drawing Sheet

(R=alkyl)

(R=alkyl)

HOMOGENEOUS α-OLEFIN DIMERIZATION CATALYSTS

The United States Government has rights in this invention pursuant to NSF Grant DE-FG86ERI3511.

This invention relates to compositions of matter useful as catalysts, to a method for preparing these catalysts, and to a method for dimerization of α-olefins utilizing the catalysts.

BACKGROUND OF THE INVENTION

The use of soluble Ziegler-Natta type catalysts in the polymerization of olefins is well known in the art. In general, such systems include a Group IV-B metal compound and a metal alkyl cocatalyst, such as an aluminum alkyl cocatalyst. More broadly, it may be said to include a mixture of a Group I–III metal alkyl and a transition metal complex from Group IVB-VB metals, particularly titanium or zirconium with aluminum alkyl cocatalysts.

Lewis acid cocatalysts such as aluminum alkyls and methylalumoxane are ubiquitous components of several important classes of highly active group alkyl-based (e.g., titanocene, zirconocene) olefin polymerization catalysts. Although electrodialysis, chemical trapping, model synthetic, XPS, surface chemical, NMR spectroscopic, and theoretical studies argue indirectly that the role of the Lewis acid is to promote (e.g., by alkide abstraction) the formation of unsaturated "cation-like" active centers (e.g., $Cp_2MR^+$, where $Cp=C_5H_5$), the exact structural nature of the catalyst-cocatalyst interaction has remained elusive.

While Ziegler-Natta type catalysts are in wide use, a continual effort is expended to improve on such catalysts to obtain better control over molecular weight and molecular weight distribution; to reduce the use of excess cocatalyst; and to permit the synthesis of small oligomers having a specific molecular weight.

Homogeneous cationic Group IV metallocene-type of complexes with the general formula $L^1L^2MR^+X^-$ ($L^1$ and $L^2$ are (substituted) cyclopentadienyl type ligands; M=Ti, Zr, Hf; R=H, Alkyl; $X^-$ is a "non-coordinating", anion derived from $B(C_6F_5)_3$, $B(C_6F_5)_4$ or methylalumoxane) have been studied extensively as olefin polymerization catalysts. Compared to traditional Ziegler-Natta catalysts, these metallocene-type catalysts have much better defined structures and chemical "tunability". For α-olefin polymerizations, the molecular weight is strongly modulated by the electronic and steric environment of the ligands.

Group IV metallocene-based α-olefin dimerization catalysts are known to include the use of metallocenes substituted and unsubstituted with alumoxanes methylalumoxane and other alkylalumoxanes, aluminum alkyl halides and a carborane anion as the cocatalyst.

SUMMARY OF THE INVENTION

Accordingly, it is an object of the subject invention to prepare and utilize a new class of olefin polymerization catalysts.

A further object of the subject invention is a catalyst which permits better control over molecular weight and molecular weight distribution.

Another object of the subject invention is a Ziegler-Natta type catalyst system which reduces the use of excess cocatalyst.

Yet another object of the subject invention is a catalyst system which is useful in the synthesis of small oligomers in a specific stereochemistry.

These and other objects are attained in the subject invention, whereby in one embodiment a strong organo-Lewis acid, a three-coordinate neutral complex such as tris(pentafluorophenyl)borane, is utilized to synthesize stoichiometrically precise, isolable/crystallographically characterizable, highly active "cation-like" metallocene polymerization catalysts. Methylalumoxanes may also be used.

$B(C_6F_5)$ reacts with Zr, Hf, Ti alkyls to yield the highly reactive cationic complex: $(L_2MR^2)^+X^-$;

where L is a substituted cyclopentadienyl ligand such as $R'_2(C_5H_3)$ where R'=a $C_3$–$C_{20}$ tert-alkyl group; $R^2$=alkyl group (C≤20), H;

where R=a $C_1$–$C_{20}$ alkyl group, H;

M=Ti, Zr, or Hf;

$X^-=RB(C_6F_5)^-_3$

As a specific example of the above, the reaction of tris(pentafluorophenyl)borane with a variety of zirconocene dimethyl complexes proceeds rapidly and quantitatively to yield, after recrystallization from hydrocarbon solvents, methyltriarylborate complexes (Eq. (1)).

$$L_2M(R)_2 + B(C_6F_5)_3 \xrightarrow{C_6H_6 \text{ or pentane}} L_2MR^+RB(C_6F_5)_3^- \quad (I)$$

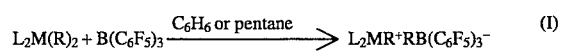

M = Zr, Ti, Hf; R = alkyl (C < 20), H.

Such catalytic complexes have been found to be active homogeneous catalysts for use at room temperature for α-olefin dimerization, and more particularly, the dimerization of α-olefins, dienes, and acetylenic monomers. By the subject invention not only may dimers be efficiently made, but better selectivity is also possible.

BRIEF DESCRIPTION OF THE DRAWINGS

These and other embodiments of the subject invention, together with additional features contributing thereto and advantages occuring therefrom will be apparent from the following description of one embodiment of the subject invention when read in conjunction with the accompanying drawings wherein.

DETAILED DESCRIPTION OF THE INVENTION

The reaction of tris(pentafluorophenyl)borane with a variety of zirconocene, titanium and hafnium complexes of the general formula $L_2MR^+_2$ (L=cyclopentadienyl ligand substituted with two —$CR_3$ groups, R=alkyl group of 1–20 carbons) proceeds rapidly and quantitatively at room temperature in noncoordinating solvents to yield, after recrystallization, methyltriarylborate complexes. This catalytic reaction may be used in the dimerization of α-olefins. As with all Ziegler-Natta type catalysts, the total exclusion of water is mandatory, and the addition of even small amounts of additional material or impurities can cause the dimerization reaction of the subject invention to fail.

In particular, certain complexes such as [1,3-$(CMe_3)_2C_5H_3]_2ZrH^+MeB$ $(C_6F_5)^+_3$, which is the reaction product of $[1,3-(CMe_3)_2C_5H_3]_2ZrMe_2$ with $B(C_6F_5)_3$ in the presence of an activating amount of hydrogen, exhibits great efficiency and selectivity for the dimerization of α-olefins including propylene, 1-butene,-1-pentene, and 1-hexene.

The subject invention disclosure involves the unique Lewis acid cocatalyst $B(C_6F_5)_3$ (or $B(C_6F_5)^-_4$) in conjunction with a very bulky bis (tertiary-alkyl) substituted cyclopentadienyl zirconocene precursor. The resulting catalyst has exceptionally high selectivity for the dimerization of a variety of α-olefins. If $B(C_6F_5)^-_4$ is utilized, the procedure is varied as follows: $L_2MR_2 + HN^+R'_3 \ B(C_6F_5)^-_4 \rightarrow L_2MR^+ \ B(C_6F_5)^-_4 + NR'_3 + Rh$ or $L^2MR_2 + (C_6F_5)_3 + CB(C_6F_5)^-_4 \rightarrow L_2MR^{+B} {}^{(C}{}_6F_5)^-_4 + RC(C_6H_5)_3$. As noted, alumoxane-(R-Al-O)$_n$, cyclic version, or R(R-Al-O)$_n$AlR$_2$, linear version, may be used as a substitute for tris(pentaflourophenyl) borane. Methylalumoxane is preferred.

The catalyst can be synthesized straightforwardly using the following procedure.

The olefin dimerization procedures are carried out under an inert atmosphere (nitrogen or argon). In a typical small scale reaction, a weighted amount of catalyst is charged into a reaction flask in a glove box at a temperature from –30° C. to 100° C. and preferably 0° C. Then a suitable amount of solvent (usually dry toluene) is added to the flask via the vacuum condensing technique. The α-olefin is either supplied continuously under 1 Atm of pressure or added in at the beginning of the reaction in a premeasured amount. The reaction products are characterized by a combination of $^1$H NMR spectroscopy and GC/MS techniques.

Figure 1:
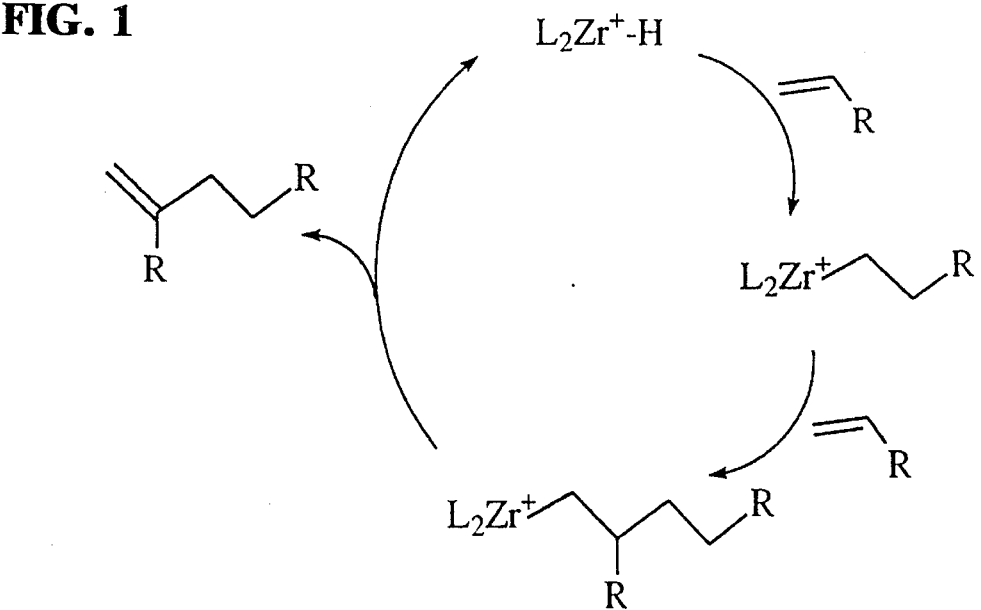
FIG. 1 is a representation of one reaction pathway of the method of the subject invention.
Figure 2:
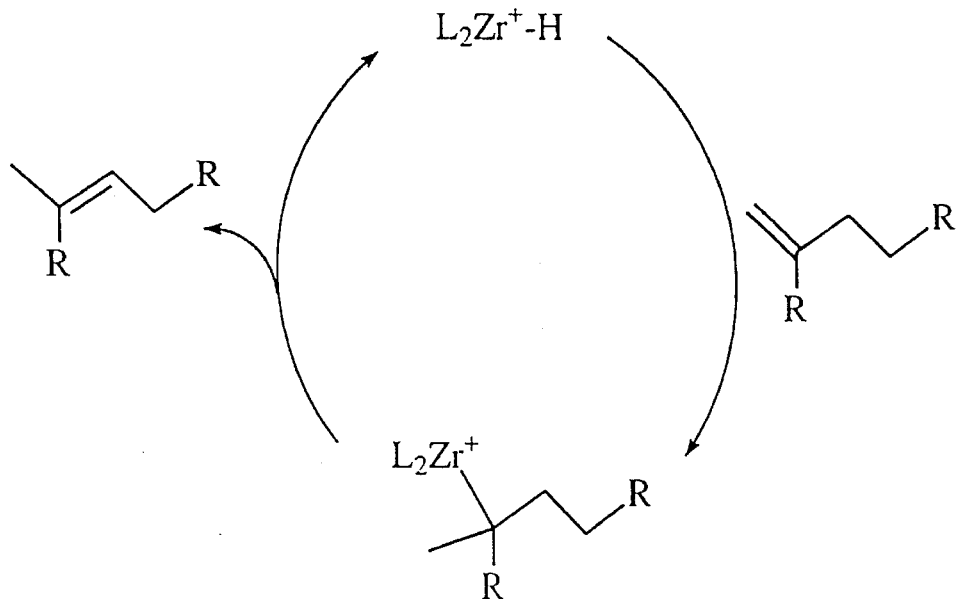
FIG. 2 is a representation of an alternative reaction pathway according to the method of the subject invention.

The primary (or major) product in all these dimerization reactions is the "head to tail" dimerization product which contains a vinylidene-type end group. This is consistent to the reaction mechanism as shown in FIG. 1. Such a product can also undergo isomerization in the presence of the same catalyst to form internal olefins which are thermodynamically favored (FIG. 2).

Example 1

Catalyst Synthesis of [1,3-$(CMe_3)_2C_5H_3]_2ZrH^+MeB(C_6F_5)^-_3$ $[1,3-(CMe_3)_2C_5H_3]_2ZrMe_2$ (0.16 g, 0.33 mmol, synthesized from the dichloride precursor by reaction with MeLi reagent) and $B(C_6F_5)_3$ (0.16 g, 0.31 mmol) were reacted in 15 mL of toluene at room temperature under 1 ATM of $H_2$ for 10 h., and the toluene was then removed. The resulting solid was washed with a small amount of pentane, collected by filtration, and dried under vacuum. Yield, 70%. Anal. Calcd. for $C_{45}H_{46}BF_{15}Zr$: C, 55.50; H, 4.70, Found: C, 55.75; H, 4.79.

Example 2

Dimerization of Propylene

In a J-Young NMR tube, a small amount of the reaction product of Example 1 was dissolved in toluene-d$_8$. The NMR tube was then filled with 1 atm of propylene. After several hours at 0° C., $^1$H NMR revealed that 2-methyl-1-pentene and 2-methyl-2-pentene (relative ration of 3 to 2) were the only two products formed. The identity of these two compounds were confirmed by comparing their $^1$H NMR data with those of known samples.

Example 3

Dimerization of Propylene

The product of Example 1, (18.5 mg, 0.020 mmol) was dissolved in 20 mL of toluene in a 50 mL flask. The solution was stirred at 0° C. under 1 atm of propylene for 90 min. The reaction was quenched by a small amount of water. Combined yield of 2-methyl-l-pentene and 2-methyl-2-pentene was 1.1 g (Estimated by weighing the reaction mixture and measuring the molar fraction of these two olefins relative to toluene by $^1$H NMR).

Example 4

Dimerization of 1-Butene

The reaction product of Example 1 (20.1 mg. 0.022 mmol) was dissolved in 20 mL of toluene in a 50 mL flask. The solution was stirred at 0° C. under 1 ATM of 1-butene for 90 min. The reaction was quenched by a small amount of water. The combined yield of 2-ethyl-1-hexene, 3-methyl-2-heptene, and 3-methyl-3-heptene was 1.3 g (Estimated by weighing the reaction mixture and measuring the molar fraction of these two olefins relative to toluene by $^1$H NMR). The molar fraction of the three species as determined by $^1$H NMR are 65%, 28%, and 7%, respectively.

Example 5

Dimerization of 1-Pentene

The reaction product of Example 1 (22.0 mg, 0.024 mmol) was dissolved in 20 mL of toluene in a 50 mL flask. Then 1-pentene (5.0 mL) was then added. The solution was stirred at 0° C. for 90 min. The reaction was quenched by a small amount of water. The combined yield of 2-propyl-1-heptene, 4-methyl-3-nonene, and 4-methyl-4-nonene was 1.4 g (Estimated by weighing the reaction mixture and measuring the molar fraction of those two olefins relative to toluene by $^1$H NMR spectroscopy). In the mixture of products, 2-propyl-1-heptene accounts for 90% and the other two products account for the remaining 10%, as determined by $^1$H NMR.

Example 6

Dimerization of 1-Hexene

The catalyst of Example 1 (23.3 mg, 0.025 mmol) was dissolved in 20 mL of toluene in a 50 mL flask. Next, 1-hexene (4.4 mL) was then added. The solution was stirred at 0° C. for 90 min. The reaction was then quenched by a small amount of water. The combined yield of 2-butyl-1-octene, 5-methyl-4-undecene and 5-methyl-5-undecene was 1.5 g (Estimated by weighing the reaction mixture and measuring the molar fraction of these two olefins relative to toluene by $^1$H NMR spectroscopy). In the mixture of products, 2-butyl-1-octene accounts for 91%, and the other two products account for the remaining 9%, as determined by $^1$H NMR.

Example 7

Catalyst With Non-substituted Cyclopentadienyl Ligands

In J-Young NMR tube, a small amount of $C_5H_5]_2ZrMe^+ MeB(C_6F_5)^-_3$ is dissolved in toluene-$d_8$. The NMR tube is then filled with 1 atm of propylene. After several hours at 0° C., $^1H$ NMR revealed that polypropylene is the primary product. The identity of this product is confirmed by $^1H$ NMR.

Example 8

Catalyst With Methyl Substituted Cyclopentadienyl Ligands

In J-Young NMR tube, a small amount of $(Me(C_5H_4)_2ZrMeMeB(C_6H_5)^-_3$ is dissolved in toluene-$d_8$. The NMR tube is then filled with 1 atm of propylene. After several hours at 0° C., $^1H$ NMR revealed that polypropylene is the primary product. The identity of this product is confirmed by $^1H$ NMR.

Example 9

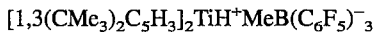

The above compound was synthesized, starting with $[1,3(CMe_3)_2C_5H_3]_2TiCl_2$ and following the procedure of Example 1.

Example 10

Dimerization of 1-Butene

The catalyst prepared in Example 9 is dissolved in 20 mL of toluene in a 50 mL flask. The solution is stirred at ° C. under 1 atm of 1-butene for 90 min. The reaction is quenched by a small amount of water. The reaction product is determined by $^1H$ NMR to be 2-ethyl-1-hexene, 3-methyl-2-heptene, and 3-methyl-3-heptene.

Example 11

$[1,3(CMe_3)_2C_5H_3]_2HfH^+MeB(C_6F_5)^-_3$ And Dimerization of 1-Butene

The above catalyst is prepared in a manner analogous to the procedure of Example 9, and is dissolved in 20 mL of toluene in a 50 mL flask. The solution is stirred at ° C. under 1 atm of 1-butene for 90 min. The reaction is quenched by a small amount of water. The reaction product is determined by $^1H$ NMR to be 2-ethyl-1-hexene, 3-methyl-2-heptene, and 3-methyl-3-heptene.

Example 12

Dimerization of 1-Hexene

The catalyst prepared in Example 10 is dissolved in 20 mL of toluene in a 50 mL flask. Next, 1-hexene is then added. The solution is stirred at 0° C. for 90 min. The reaction is then quenched by a small amount of water. The product is determined by $^1H$ NMR to be 2-butyl-1-octene, 5-methyl-4-undecene and 5-methyl-5-undecene.

It is noted from the above that only bis-tertalkyl substitutions on the cyclopentadienyl rings resulted in dimers. All other substitutions and nonsubstitutions result in polymers.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed:

1. A catalytic complex consisting essentially of the structure:

$(L_2MR')^+X^-$ where

L=$R_2(C_5H_3)$; R=a $C_3$–$C_{20}$ tert-alkyl; R'=a $C_1$–$C_{20}$ alkyl group or H;

M=Ti, Zr or Hf;

X$^-$=$RB(C_5F_3)_3$, or the negative anion of methylalumoxane, where RA=a $C_1$–$C_{20}$ alkyl group or H;

2. The catalytic complex of claim 1 wherein R is a tert-butyl group.

* * * * *

UNITED STATES PATENT AND TRADEMARK OFFICE
CERTIFICATE OF CORRECTION

PATENT NO. : 5,500,398            Page 1 of 2
DATED      : March 19, 1996
INVENTOR(S) : Marks et al.

It is certified that error appears in the above-indentified patent and that said Letters Patent is hereby corrected as shown below:

IN THE ABSTRACT:

Line 9:              "$RB(C_3F_3)^-_3$" should read --$R''B(C_6F_5)^-_3$--

Column 1   Line 42   Delete "," after "'non-coordinating'"

Column 2   Line 66   "$(C_6F_5)^+_3$" should read --$(C_6F_5)^-_3$--

Column 3   Line 11   "$^{B/C}_6F_5)^-_4$ [1st instance] should read --$B(C_6F_5)^-_4$--
                     Rh should read --RH--
                     $L^2MR_2$ should read --$L_2MR_2$--

Column 3   Line 12   "$L_2MR^{+B/C}_6F_5)^-4$" should read --$L_2MR^+B(C_6F_5)^-_4$--

Column 5   Line 36   "°C" should read --0°C--

Column 5   Line 48   "°C" should read --0°C--

IN THE CLAIMS:

Column 6   Line 42   "$RB(C_5F_3)_3$" should read --$R''B(C_6F_5)^-_3$--

UNITED STATES PATENT AND TRADEMARK OFFICE
CERTIFICATE OF CORRECTION

PATENT NO. : 5,500,398
DATED : March 19, 1996
INVENTOR(S) : Marks et al.

It is certified that error appears in the above-indentified patent and that said Letters Patent is hereby corrected as shown below:

Column 6    Line 43    "RΔ" should read --R"--

Signed and Sealed this

Thirteenth Day of May, 1997

Attest:

BRUCE LEHMAN

Attesting Officer    Commissioner of Patents and Trademarks